(12) United States Patent
Hile

(10) Patent No.: US 8,519,236 B1
(45) Date of Patent: Aug. 27, 2013

(54) INBRED CORN LINE NPFF6228

(75) Inventor: Glenn Hile, Fort Wayne, IN (US)

(73) Assignee: Syngenta Participations AG, Basel (CH)

( * ) Notice: Subject to any disclaimer, the term of this patent is extended or adjusted under 35 U.S.C. 154(b) by 621 days.

(21) Appl. No.: 12/713,511

(22) Filed: Feb. 26, 2010

(51) Int. Cl.
*A01H 5/00* (2006.01)
*C12N 15/82* (2006.01)

(52) U.S. Cl.
USPC ........ 800/320.1; 800/260; 800/278; 800/275; 435/415

(58) Field of Classification Search
USPC ...................................... 800/320.1
See application file for complete search history.

(56) References Cited

U.S. PATENT DOCUMENTS

| 6,156,957 | A | 12/2000 | Krier |
| 7,122,726 | B2 | 10/2006 | Mousel |
| 7,659,456 | B2 * | 2/2010 | Holthaus ................ 800/320.1 |

* cited by examiner

*Primary Examiner* — Li Zheng
(74) *Attorney, Agent, or Firm* — Dale Skalla

(57) ABSTRACT

Basically, this invention provides for an inbred corn line designated NPFF6228, methods for producing a corn plant by crossing plants of the inbred line NPFF6228, with plants of another corn plant. The invention relates to the various parts of inbred NPFF6228, including culturable cells. This invention also relates to methods for introducing transgenic transgenes into inbred corn line NPFF6228, and plants produced by said methods.

19 Claims, No Drawings

INBRED CORN LINE NPFF6228

FIELD OF THE INVENTION

This invention is in the field of corn breeding. The invention relates to a maize and it s seed designated NPFF6228, derivatives and hybrids thereof. This invention also is in the field of hybrid maize production employing the present inbred.

BACKGROUND OF THE INVENTION

Corn plants (*Zea mays* L.) can be self-pollinating or cross pollinating. Self pollination for extended time periods produces homozygousity at almost all gene loci, forming a uniform population of true breeding progeny. These are inbreds. Crossing two homozygous inbreds produces heterozygous gene loci in hybrid plants and seeds.

Maize plant breeding is a process to develop improved maize germplasm in an inbred or hybrid. Hybrids are developed with inbreds which are developed by selecting corn lines and self pollinating these lines for several generations to develop homozygous pure inbred lines. Two inbred lines are crossed and hybrid seed is produced. One inbred is emasculated and the pollen from the other inbred pollinates the emasculated inbred. The emasculated inbred, often referred to as the female, produces the hybrid seed F1. Emasculation of the inbred can be done by detasseling the seed parent, or the inbred could have a male sterility factor which would eliminate the need to detassel the inbred.

Whether the seed producing plant is emasculated due to detasseling or CMS or transgenes, the seed produced by crossing two inbreds in this manner is hybrid seed. This hybrid seed is F1 hybrid seed. The grain produced by a plant grown from a F1 hybrid seed is referred to as F2 or grain. Although, all F1 seed and plants, produced by this hybrid seed production system using the same two inbreds should be substantially the same, all F2 grain produced from the F1 plant will be segregating maize material.

The hybrid seed production produces hybrid seed which is heterozygous. The heterozygosis results in hybrid plants, which are robust and vigorous plants. Inbreds on the other hand are mostly homozygous. This homozygosity renders the inbred lines less vigorous. Inbred seed can be difficult to produce since the inbreeding process in corn lines decreases the vigor. However, when two inbred lines are crossed, the hybrid plant evidences greatly increased vigor and seed yield compared to open pollinated, segregating maize plants. An important consequence of the homozygosity and the homogenity of the inbred maize lines is that all hybrid seed produced from any cross of two such elite lines will be the same hybrid seed and make the same hybrid plant. Thus the use of inbreds makes hybrid seed which can be reproduced readily.

The ultimate objective of the commercial maize seed companies is to produce high yielding, agronomically sound plants that perform well in certain regions or areas of the Corn Belt.

SUMMARY OF THE INVENTION

The present invention relates to an inbred corn line NPFF6228. Specifically, this invention relates to plants and seeds of this line. Additionally, this relates to a method of producing from this inbred, hybrid seed corn and hybrid plants with seeds from such hybrid seed. More particularly, this invention relates to the unique combination of traits that combine in corn line NPFF6228.

Generally then, broadly the present invention includes an inbred corn seed designated NPFF6228. This seed produces a corn plant.

The invention also includes the tissue culture of regenerable cells of NPFF6228, wherein the cells of the tissue culture regenerates plants capable of expressing the genotype of NPFF6228. The tissue culture is selected from the group consisting of leaf, pollen, embryo, root, root tip, guard cell, ovule, seed, anther, silk, flower, kernel, ear, cob, husk and stalk, cell and protoplast thereof. The corn plant regenerated from NPFF6228 or any part thereof is included in the present invention. The present invention includes regenerated corn plants that are capable of expressing NPFF6228's genotype, phenotype or mutants or variants thereof.

The invention extends to hybrid seed produced by planting, in pollinating proximity which includes using preserved maize pollen as explained in U.S. Pat. No. 5,596,838 to Greaves, seeds of corn inbred lines NPFF6228 and another inbred line if preserved pollen is not used; cultivating corn plants resulting from said planting; preventing pollen production by the plants of one of the inbred lines if two are employed; allowing cross pollination to occur between said inbred lines; and harvesting seeds produced on plants of the selected inbred. The hybrid seed produced by hybrid combination of plants of inbred corn seed designated NPFF6228 and plants of another inbred line are a part of the present invention. This inventions scope covers hybrid plants and the plant parts including the grain and pollen grown from this hybrid seed.

The invention further includes a method of hybrid F1 production. A first generation (F1) hybrid corn plant produced by the process of planting seeds of corn inbred line NPFF6228; cultivating corn plants resulting from said planting; permitting pollen from another inbred line to cross pollinate inbred line NPFF6228; harvesting seeds produced on plants of the inbred; and growing a harvested seed are part of the method of this invention.

The present invention also encompasses a method of introducing at least one targeted trait into maize inbred line comprising the steps of: (a) crossing plant grown from the present invention seed which is the recurrent parent, representative seed of which has been deposited, with the donor plant of another maize line that comprises at least one target trait selected from the group consisting of male sterility, herbicide resistance, insect resistance, disease resistance, amylose starch, and waxy starch to produce F1 plants; (b) selecting from the F1 plants that have at least one of the targeted traits, forming a pool of progeny plants with the targeted trait; (c) crossing the pool of progeny plants with the present invention which is the recurrent parent to produce backcrossed progeny plants with the targeted trait; (d) selecting for backcrossed progeny plants that have at least one of the target traits and physiological and morphological characteristics of maize inbred line of the recurrent parent, listed in Table 1 forming a pool of selected backcrossed progeny plants; and (e) crossing the selected backcrossed progeny plants to the recurrent parent and selecting from the resulting plants for the targeted trait and physiological and morphological characteristics of maize inbred line of the recurrent parent, listed in Table 1 and reselecting from the pool of resulting plants and repeating the crossing to the recurrent parent and selecting step in succession to form a plant that comprises the desired trait and all of the physiological and morphological characteristics of maize inbred line of the recurrent parent in the present invention listed in Table 1 as determined at the 5% significance level when grown in the same environmental conditions.

This method and the following method of introducing traits can be done with less back crossing events if the trait and/or the genotype of the present invention are selected for or identified through the use of markers. SSR, microsatellites, SNP and the like decrease the amount of breeding time required to locate a line with the desired trait or traits and the characteristics of the present invention. Backcrossing in two or even three traits (for example the glyphosate, Europe corn borer, corn rootworm resistant genes) is routinely done with the use of marker assisted breeding techniques. This introduction of transgenes or mutations into a maize line is often called single gene conversion. Although, presently more than one gene particularly transgenes or mutations which are readily tracked with markers can be moved during the same "single gene conversion" process, resulting in a line with the addition of more targeted traits than just the one, but still having the characteristics of the present invention plus those characteristics added by the targeted traits.

The method of introducing a desired trait into maize inbred line comprising: (a) crossing plant grown from the present invention seed, representative seed of which has been deposited the recurrent parent, with plant of another maize line that comprises at least one target trait selected from the group consisting of nucleic acid encoding an enzyme selected from the group consisting of phytase, stearyl-ACP desaturase, fructosyltransferase, levansucrase, amylase, invertase and starch branching enzyme, the donor parent to produce F1 plants; (b) selecting for the targeted trait from the F1 plants, forming a pool of progeny plants; (c) crossing the progeny plants with the recurrent parent to produce backcrossed progeny plants; (d) selecting for backcrossed progeny plants that have at least one of the target trait and physiological and morphological characteristics of maize inbred line of the present invention as listed in Table 1 forming a pool of backcrossed progeny plants; and repeating a step of crossing the new pool with the recurrent parent and selecting for the targeted trait and the recurrent parents characteristics until the selected plant is essentially the recurrent parent with the targeted trait or targeted traits. This selection and crossing may take at least 4 backcrosses if marker assisted breeding is not employed.

The inbred line and seed of the present invention are employed to carry the agronomic package into the hybrid. Additionally, the inbred line is often carrying transgenes that are introduced in to the hybrid seed.

Likewise included is a first generation (F1) hybrid corn plant produced by the process of planting seeds of corn inbred line NPFF6228; cultivating corn plants resulting from said planting; permitting pollen from inbred line NPFF6228 to cross pollinate another inbred line; harvesting seeds produced on plants of the inbred; and growing a plant from such a harvested seed.

A number of different techniques exist which are designed to avoid detasseling in maize hybrid production. Some examples are switchable male sterility, lethal genes in the pollen or anther, inducible male sterility, male sterility genes with chemical restorers. There are numerous patented means of improving upon the hybrid production system. Some examples include U.S. Pat. No. 6,025,546, which relates to the use of tapetum-specific promoters and the barnase gene to produce male sterility; U.S. Pat. No. 6,627,799 relates to modifying stamen cells to provide male sterility. Therefore, one aspect of the current invention concerns the present invention comprising one or more gene(s) capable of restoring male fertility to male-sterile maize inbreds or hybrids and/or genes or traits to produce male sterility in maize inbreds or hybrids.

The inbred corn line NPFF6228 and at least one transgenic gene adapted to give NPFF6228 additional and/or altered phenotypic traits are within the scope of the invention. Such transgenes are usually associated with regulatory elements (promoters, enhancers, terminators and the like). Presently, transgenes provide the invention with traits such as insect resistance, herbicide resistance, disease resistance increased or decreased starch or sugars or oils, increased or decreased life cycle or other altered trait.

The present invention includes inbred corn line NPFF6228 and at least one transgenic gene adapted to give NPFF6228 modified starch traits. Furthermore this invention includes the inbred corn line NPFF6228 and at least one mutant gene adapted to give modified starch, acid or oil traits, i.e. amylase, waxy, amylose extender or amylose. The present invention includes the inbred corn line NPFF6228 and at least one transgenic gene: *bacillus thuringiensis*, the bar or pat gene encoding Phosphinothricin acetyl Transferase, Gdha gene, GOX, VIP, EPSP synthase gene, low phytic acid producing gene, and zein. The inbred corn line NPFF6228 and at least one transgenic gene useful as a selectable marker or a screenable marker is covered by the present invention.

A tissue culture of the regenerable cells of hybrid plants produced with use of NPFF6228 genetic material is covered by this invention. A tissue culture of the regenerable cells of the corn plant produced by the method described above is also included.

DEFINITIONS

In the description and examples, which follow, a number of terms are used. In order to provide a clear and consistent understanding of the specifications and claims, including the scope to be given such terms, the following definitions are provided.

ALLELE—Any alternative forms of sequence. Diploid cells carry two alleles of the genetic sequence. These two sequence alleles correspond to the same locus (i.e. position) on homologous chromosomes.

ELITE INBRED—Maize plant that is substantially homozygous and which contributes useful agronomic and/or phenotypic qualities when used to produce hybrids that are commercially acceptable.

GENE SILENCING—The loss or inhibition of the expression of a gene.

GENOTYPE—genetic makeup.

LINKAGE—Refers to a tendency of a segment of DNA on the same chromosome to not separate during meiosis of homologous chromosomes. Thus during meiosis this segment of DNA remains unbroken more often than expected by chance.

LINKAGE DISEQUILIBRIUM—Alleles tendency to remain in linked groups when segregating from parents to progeny, than expected from chance.

LOCUS—A defined segment of DNA. This segment is often associated with an allele position on a chromosome.

PHENOTYPE—The detectible characteristics of the maize plant. These characteristics often are detections of the genotype/environment interaction.

PLANT—this includes reference to an immature or mature whole plant, including a plant that has been detasseled or from which seed or grain has been removed. Seed or embryo that will produce the plant is also considered to be the plant.

Early Season Trait Codes

Emergence Rating (EMRGR): Recorded when 50% of the plots in the trial are at V1 (1 leaf collar) growth stage.
  1=All plants have emerged and are uniform in size
  3=All plants have emerged but are not completely uniform
  5=Most plants have emerged with some just beginning to break the soil surface, noticeable lack of uniformity 7=Less than 50% of the plants have emerged, and lack of uniformity is very noticeable 9=A few plants have emerged but most remain under the soil surface.

Seedling Growth (SVGRR or Vigor): Recorded between V3 and V5 (3-5 leaf stage) giving greatest weight to seedling plant size and secondary weight to uniform growth.
- 1=Large plant size and uniform growth
- 3=Acceptable plant size and uniform growth
- 5=Acceptable plant size and might be a little non-uniform
- 7=Weak looking plants and non-uniform growth
- 9=Small plants with poor uniformity Purpling (PRPLR): Emergence and/or early growth rating. Purpling is more pronounced on the under sides of leaf blades especially on midribs.
- 1=No plants showing purple color
- 3=30% plants showing purple color
- 5=50% plants showing purple color
- 7=70% plants showing purple color
- 9=90+% plants showing purple color Herbicide Injury (HRBDR) List the herbicide type, which is being rated. Then rated each hybrid/variety injury as indicated below.
- 1=No apparent reduction in biomass or other injury symptoms
- 5=Moderate reduction in biomass with some signs of sensitivity
- 9=Severe reduction in biomass with some mortality Mid-Season Traits Codes Heat Units to 50% Silk (HUPSN): Recorded the day when 50% of all plants within a plot show 2 cm or more silk protruding from the ear. Converted days to accumulated heat units from planting.

Heat units to 50% Pollen Shed (HUPSN): Recorded the day when 50% of all plants within a plot are shedding pollen. Converted days to accumulated heat units from planting.

Plant Height (PLHTN): After pollination, recorded average plant height of each plot. Measured from ground to base of leaf noted.

Plant Ear Height (ERHTN): After pollination record average ear height of each plot. Measure from ground to base of ear node (shank).—for Inbreds Plant Ear Height in CM: After pollination record average ear height of each plot. Measure from ground to base of ear node (shank).—for Hybrids Root Lodging Early % (ERTLP): Early root lodging occurs up to about two weeks after flowering and usually involves goosenecking. The number of root lodged plants are counted and converted to percentage.

Shed Duration (Shed Duration): Sum of daily heatunits for days when plants in the plot are actively shedding pollen.

Foliar Disease (LFDSR): Foliar disease ratings taken one month before harvest through harvest. The predominant disease should be listed in the trial information and individual hybrid ratings should be given.
- 1=No lesions to two lesions per leaf.
- 3=A few scattered lesions on the leaf. About five to ten percent of the leaf surface is affected.
- 5=A moderate number of lesions are on the leaf. About 15 to 20 percent of the leaf surface is affected.
- 7=Abundant lesions are on the leaf. About 30 to 40 percent of the leaf surface is affected.
- 9=Highly abundant lesions (>50 percent) on the leaf. Lesions are highly coalesced. Plants may be prematurely killed.

Data collection (as described above) on the following diseases:

| | |
|---|---|
| Common Rust (CR) | Eye Spot (ES) |
| Gray Leaf Spot (GLS) | Northern Corn Leaf Blight (NCLB) |
| Stewart's Bacterial Wilt (SBW) | Southern Corn Leaf Blight (SCLB) |
| Southern Rust (SR) | Corn Virus Complex (CVC) |

Maize response to diseases can also be rated as:
- R=Resistant=1 to 2 rating
- MR=Moderately Resistant=3 to 4 rating
- MS=Moderately Susceptible=5 to 6 rating
- S=Susceptible=7 to 9 rating Preharvest Trait Codes Heat units to Black Layer (HUBLN): The day when 50% of all plants within a plot reach black layer stage is recorded. Convert days to accumulated heat units from planting.

Harvest Population (HAVPN): The number of plants in yield rows, excluding tillers, in each plot are counted.

Barren Plants (BRRNP): The number of plants in yield rows having no ears and/or abnormal ears with less than 50 kernels are counted.

Dropped Ears (DROPP): The numbers of ears lying on the ground in yield rows are counted.

Stalk Lodging % (STKLP): Stalk lodging will be reported as number of plants broken below the ear without pushing, excluding green snapped plants. The number of broken plants in yield rows are counted and converted to percent.

Root Lodging Late % (LRTLP): Late root lodging can usually start to occur about two weeks after flowering and involves lodging at the base of the plant. Plants leaning at a 30-degree angle or more from the vertical are considered lodged. The number of root lodged plants in yield rows are counted and converted to percent.

Push Test for Stalk and Root Quality on Erect Plants % (PSTSP or PCT Push or % Pushtest): The push test is applied to trials with approximately five percent or less average stalk lodging. Plants are pushed that are not root lodged or broken prior to the push test. Standing next to the plant, the hand is placed at the top ear and pushed to arm's length. Push one of the border rows (four-row small plot) into an adjacent plot border row. The number of plants leaning at a 30-degree angle or more from the vertical, including plants with broken stalks prior to pushing are counted. Plants that have strong rinds that snap rather than bend over easily are not counted. The goal of the push test is to identify stalk rot and stalk lodging potential, NOT ECB injury.

PUSXN: Push ten plants and enter the number of plants that do not remain upright.

Intactness (INTLR):
- 1=Healthy appearance, tops unbroken
- 5=25% of tops broken
- 9=majority of tops broken Plant Appearance (PLTAR): This is a visual rating based on general plant appearance taking into account all factors of intactness, pest, and disease pressure.
- 1=Complete plant with healthy appearance
- 5=plants look OK
- 9=Plants not acceptable Green Snap (GRSNP or PCTGS or % GreenSnap): Counted the number of plants in yield rows that snapped below the ear due to brittleness associated with high winds.

Stay-green (STGRP): This is an assessment of the ability of a grain hybrid to retain green color as maturity approaches (taken near the time of black-layer) and should not be a reflection of hybrid maturity or leaf disease. Recorded % of green tissue. This may be listed as a Stay Green Rating instead of a Percentage.

Stay Green Rating (STGRR): This is an assessment of the ability of a grain hybrid to retain green color as maturity approached (taken near the time of black layer or if major differences are noted later). This rating should not be a reflection of the hybrid maturity or leaf disease.
    1=solid Green Plant
    9=no green tissue
Ear/Kernel Rots (KRDSR): If ear or kernel rots are present, husk ten consecutive ears in each plot and count the number that have evidence of ear or kernel rots, multiply by 10, and round up to the nearest rating as described below. Identify and record the disease primarily responsible for the rot.
    1=No rots, 0% of the ears infected.
    3=Up to 10% of the ears infected.
    5=11 to 20% of the ears infected.
    7=21 to 35% of the ears infected.
    9=36% or more of the ears infected.
Grain Quality (GRQUR): Taken on husked ears after black layer stage. The kernel cap integrity and relative amount of soft starch endosperm along the sides of kernels is rated.
    1=smooth kernel caps and or 10% or less soft starch
    3=slight kernel wrinkles and or 30% soft starch
    7=moderate kernel wrinkles and or 70% soft starch
    9=severe kernel wrinkled and or 90% or more soft starch
Preharvest Hybrid Characteristics
Ear Shape (DESHR): Slender, Semi-Blocky, Blocky
    1=Blocky
    5=Semi-blocky
    9=Slender
Ear Type (EARFR): Fixed, Semi-Fixed, Flex
    1=Flex
    5=Semi-flex
    9=Fixed
Husk Cover (HSKCR): Short, Medium, Long
    1=Long
    5=Medium
    9=Short
Kernel Depth (KRLNR): Shallow, Medium, Deep
    1=Deep
    5=Medium
    9=Short (shallow)
Shank Length (SHLNR): Short, Medium, Long
    1=Short
    5=Medium
    9=Long
Kernel Row Number (KRRWN): The average number of kernel rows on 3 ears.
Cob diameter (COBDR): Cob diameter is to be taken with template.
    1: small
    5: Medium
    9: Large
Harvest Trait Codes
Number of Rows Harvested (NRHAN)
Plot Width (RWIDN)
Plot Length (RLENN)
Yield Lb/Plot (YGSMN): bushels per acre adjusted to 15.5% moisture
Test Weight (TSTWN or TWT): test weight at harvest in pounds per bushel
Moisture % (MST_P): percent moisture or grain at harvest
Adjusted Yield in Bu/A (YBUAN)
Color Codes
Kernel Type: (KRTPN)
    1) Dent
    2) Flint Endosperm Type: (KRTEN)
    1) normal
    2) amylose
    3) waxy
    4) other
Sterile Type (MSCT):
    1) no
    if yes cytoplasm type then:
    2) c-type
    3) s-type
Anthocyanin of Brace Roots (PBRCC): the presence of color on 60% of the brace roots during pollen shed.
    1) Absent
    2) Faint
    3) Moderate
    4) Dark
    5) Brace Roots not present
    6) Green
    7) Red
    8) Purple
Anther Color (ANTCC): at 50 percent pollen shed observe the color of newly extruded anthers, pollen not yet shed
    1) Yellow
    2) Red
    3) Pink
    4) Purple
Glume Color (GLMCC): color of glumes prior to pollen shed
    1) Red
    2) Green
Silk Color (SLKCC): Taken at a late flowering stage when all plants have fully extruded silk. Silks at least 2" long but still fresh.
    1) Yellow
    2) Pink
    3) Red
Kernel Color (KERCC): the main color of the kernel from at least three ears per ear family.
    1) Yellow
    2) White
Cob Color (COBCC): the main color of the cob after shelling from at least three ears per ear family.
    1) Red
    2) Pink
    3) White

| ABR. | Description | Input Value |
|---|---|---|
| EMRGN | Final number of plants per plot | # |
| REGNN | Region Developed: 1. Northwest 2. Northcentral 3. Northeast 4. Southeast 5. Southcentral 6. Southwest 7. Other | # |
| CRTYN | Cross type: 1. sc 2. dc 3. 3w 4. msc 5. m3w 6. inbred 7. rel. line 8. other | # |
| KRTPN | Kernel type: 1. sweet 2. dent 3. flint 4. flour 5. pop 6. ornamental 7. pipecorn 8. other | # |
| EMERN | Days to Emergence EMERN | # Days |
| ERTLP | % Root lodging: (before anthesis): | #% |
| GRSNP | % Brittle snapping: (before anthesis): | #% |
| TBANN | Tassel branch angle of 2nd primary lateral branch at anthesis: | degree |
| HUPSN | Heat units to 50% pollen shed: (from emergence) | # HU |
| SLKCN | Silk color: | #/Munsell value |
| HU5SN | Heat units to 50% silk: (from emergence) | # HU |
| DSAZN | Days to 50% silk in adapted zone: | # Days |
| HU9PN | Heat units to 90% pollen shed: (from emergence) | # HU |
| HU19N | Heat units from 10% to 90% pollen shed: | # HU |
| DA19N | Days from 10% to 90% pollen shed: | # Days |

-continued

| ABR. | Description | Input Value |
|---|---|---|
| LSPUR | Leaf sheath pubescence of second leaf above the ear (at anthesis) 1-9 (1 = none): | # |
| ANGBN | Angle between stalk and 2nd leaf above the ear (at anthesis): | degree |
| CR2LN | Color of 2nd leaf above the ear (at anthesis): | #/Munsell value |
| GLCRN | Glume Color: | #/Munsell value |
| GLCBN | Glume color bars perpendicular to their veins (glume bands): 1. absent 2. present | # |
| ANTCN | Anther color: | #/Munsell value |
| PLQUR | Pollen Shed: 1-9 (0 = male sterile) | # |
| HU1PN | Heat units to 10% pollen shed: (from emergence) | # HU |
| LAERN | Number of leaves above the top ear node: | # |
| LTBRN | Number of lateral tassel branches that originate from the central spike: | # |
| EARPN | Number of ears per stalk: | # |
| APBRR | Anthocyanin pigment of brace roots: 1. absent 2. faint 3. moderate 4. dark | # |
| TILLN | Number of tillers: | # |
| HSKCN | Husk color 25 days after 50% silk: (fresh) | #/Munsell value |
| MLWVR | Leaf marginal waves: 1-9 (1 = none) | # |
| LFLCR | Leaf longitudinal creases: 1-9 (1 = none) | # |
| ERLLN | Length of ear leaf at the top ear node: | # cm |
| ERLWN | Width of ear leaf at the top ear node at the widest point: | # cm |
| PLHTN | Plant height to tassel tip: | # cm |
| ERHCN | Plant height to the top ear node: | # cm |
| LTEIN | Length of the internode between the ear node and the node above: | # cm |
| LTASN | Length of the tassel from top leaf collar to tassel tip: | # cm |
| HSKDN | Husk color 65 days after 50% silk: (dry) | #/Munsell value |
| DSGMN | Days from 50% silk to 25% grain moisture in adapted zone: | # Days |
| SHLNN | Shank length: | # cm |
| ERLNN | Ear length: | # cm |
| ERDIN | Diameter of the ear at the midpoint: | # mm |
| EWGTN | Weight of a husked ear: | # gm |
| KRRWR | Kernel rows: l. indistinct 2. distinct | # |
| KRNAR | Kernel row alignment: 1. straight 2. slightly curved 3. curved | # |
| ETAPR | Ear taper: 1. slight 2. average 3. extreme | # |
| KRRWN | Number of kernel rows: | # |
| COBCN | Cob color: | #/Munsell value |
| HSKTR | Husk tightness 65 days after 50% silk: 1-9 (1 = loose) | # |
| COBDN | Diameter of the cob at the midpoint: | # mm |
| YBUAN | Yield: | # kg/ha |
| KRTEN | Endosperm type: 1. sweet 2. extra sweet 3. normal 4. high amylose 5. waxy 6. high protein 7. high lysine 8. super sweet 9. high oil 10. other | 3 |
| KRCLN | Hard endosperm color: | #/Munsell value |
| ALECN | Aleurone color: | #/Munsell value |
| ALCPR | Aleurone color pattern: 1. homozygous 2. segregating | # |
| KRLNN | Kernal length: | # mm |
| KRWDN | Kernel width: | # mm |
| KRDPN | Kernel thickness: | # mm |
| K1KHN | 100 kernel weight: | # gm |
| HSKCR | Husk extension: 1. short (ear exposed) 2. medium (8 cm) 3. long (8-10 cm) 4. very long (>10 cm) | # |
| KRPRN | % round kernels on 13/64 slotted screen: | #% |
| HEPSR | Position of ear 65 days after 50% silk: 1. upright 2. horizontal 3. pendent | # |
| STGRP | Staygreen 65 days after anthesis: 1-9 (1 = worst) | # |
| DPOPP | % dropped ears 65 days after anthesis: | % |
| LRTRP | % root lodging 65 days after anthesis: | % |
| HU25N | Heat units to 25% grain moisture: (from emergence) | # HU |
| HUSGN | Heat units from 50% silk to 25% grain moisture in adapted zone: | # HU |

DETAILED DESCRIPTION OF THE INVENTION

The inbred provides uniformity and stability within the limits of environmental influence for traits as described in the Variety Description Information (Table 1) that follows.

Male sterility and/or CMS systems for maize parallel the CMS type systems that have been routinely used in hybrid production in sunflower.

To produce these types of hybrids, the companies must develop inbreds, which carry needed traits into the hybrid combination. Hybrids are not often uniformly adapted for the entire Corn Belt, but most often are specifically adapted for regions of the Corn Belt. Northern regions of the Corn Belt require shorter season hybrids than do southern regions of the Corn Belt. Hybrids that grow well in Colorado and Nebraska soils may not flourish in richer Illinois and Iowa soils. Thus, a variety of major agronomic traits is important in hybrid combination for the various Corn Belt regions, and has an impact on hybrid performance.

Inbred line development and hybrid testing have been emphasized in the past half-century in commercial maize production as a means to increase hybrid performance. Inbred development can be by pedigree selection, haploid/dihaploid production, and recurrent selection. Pedigree selection can be the selection in an F2 population produced from a planned cross of two genotypes (often elite inbred lines), or selection of progeny of synthetic varieties, open pollinated, composite, or backcrossed populations. This type of selection is effective for highly inheritable traits, but other traits, for example, yield requires replicated test crosses at a variety of stages for accurate selection.

Maize breeders select for a variety of traits in inbreds that impact hybrid performance along with selecting for acceptable parental traits. Such traits include but are not limited to: yield potential in hybrid combination, dry down, maturity, grain moisture at harvest, greensnap, resistance to root lodging, resistance to stalk lodging, grain quality, disease and insect resistance, ear, and plant height. Additionally, hybrid performance will differ in different soil types such as low levels of organic matter, clay, sand, black, high pH, low pH; or in different environments such as wet environments, drought environments, and no tillage conditions. These traits appear to be governed by a complex genetic system that makes selection and breeding of an inbred line extremely difficult. Even if an inbred in hybrid combination has excellent yield (a desired characteristic), it may not be useful because it fails to have acceptable parental traits such as seed yield, seed size, pollen production, good silks, plant height, etc.

To illustrate the difficulty of breeding and developing inbred lines, the following example is given. Two inbreds compared for similarity of 29 traits differed significantly for 18 traits between the two lines. If 18 simply inherited single gene traits were polymorphic with gene frequencies of 0.5 in the parental lines, and assuming independent segregation (as would essentially be the case if each trait resided on a different chromosome arm), then the specific combination of these traits as embodied in an inbred would only be expected to become fixed at a rate of one in 262,144 possible homozygous genetic combinations. Selection of the specific inbred combination is also influenced by the specific selection environment on many of these 18 traits which makes the probability of obtaining this one inbred even more remote. In addition, most traits in the corn genome are regrettably not single dominant genes but are multi-genetic with additive gene action not dominant gene action. Thus, the general procedure of producing a non segregating F1 generation and self pollinating to produce a F2 generation that segregates for traits and selecting progeny with the visual traits desired does not easily lead to an useful inbred. Great care and breeder expertise must be used in selection of breeding material to continue to increase yield and the agronomics of inbreds and resultant commercial hybrids.

Certain regions of the Corn Belt have specific difficulties that other regions may not have. Thus the hybrids developed from the inbreds have to have traits that overcome or at least minimize these regional growing problems. Examples of these problems include in the eastern corn belt Gray Leaf Spot, in the north cool temperatures during seedling emergence, in the Nebraska region CLN (Corn Lethal Necrosis) and in the west soil that has excessively high pH levels. The industry often targets inbreds that address these issues specifically forming niche products. However, the aim of most large seed producers is to provide a number of traits to each inbred so that the corresponding hybrid can be useful in broader regions of the Corn Belt. The new biotechnology techniques such as Microsatellites, RFLPs, RAPDs and the like have provided breeders with additional tools to accomplish these goals.

The inbred has been produced through a dihaploid system or is self-pollinated for a sufficient number of generations to give inbred uniformity. During plant selection in each generation, the uniformity of plant type was selected to ensure homozygosity and phenotypic stability. The line has been increased in isolated farmland environments with data on uniformity and agronomic traits being observed to assure uniformity and stability. No variant traits have been observed or are expected in NPFF6228.

The best method of producing the invention is by planting the seed of NPFF6228 which is substantially homozygous and self-pollinating or sib pollinating the resultant plant in an isolated environment, and harvesting the resultant seed.

In the standard CMS system there are three different maize lines required to make the hybrid. First, there is a cytoplasmic male-sterile line usually carrying the CMS or some other form of male sterility. This line will be the seed producing parent line. Second, there must be a fertile inbred line that is the same or isogenic with the seed producing inbred parent but lacking the trait of male sterility. This is a maintainer line needed to make new inbred seed of the seed producing male sterile parent. Third there is a different inbred which is fertile, has normal cytoplasm and carries a fertility restoring gene. This line is called the restorer line in the CMS system. The CMS cytoplasm is inherited from the maternal parent (or the seed producing plant); therefore for the hybrid seed produced on such plant to be fertile the pollen used to fertilize this plant must carry the restorer gene. The positive aspect of this is that it allows hybrid seed to be produced without the need for detasseling the seed parent. However, this system does require breeding of all three types of lines: 1) male sterile-to carry the CMS, 2) the maintainer line; and, 3) the line carrying the fertility restorer gene.

In some instances, sterile hybrids are produced and the pollen necessary for the formation of grain on these hybrids is supplied by interplanting of fertile inbreds in the field with the sterile hybrids.

A number of different inventions exist which are designed to avoid detasseling in maize hybrid production. Some examples are switchable male sterility, lethal genes in the pollen or anther, inducible male sterility, male sterility genes with chemical restorers, sterility genes linked with a parent. U.S. Pat. No. 6,025,546, relates to the use of tapetum-specific promoters and the barnase gene. U.S. Pat. No. 6,627,799 relates to modifying stamen cells to provide male sterility. Therefore, one aspect of the current invention concerns the present invention comprising one or more gene(s) capable of restoring male fertility to male-sterile maize inbreds or hybrids.

This invention also is directed to methods for producing a corn plant by crossing a first parent corn plant with a second parent corn plant wherein the first or second parent corn plant is an inbred corn plant from the line NPFF6228. Further, both first and second parent corn plants can come from the inbred corn line NPFF6228 which produces a self of the inbred invention. The present invention can be employed in a variety of breeding methods which can be selected depending on the mode of reproduction, the trait, and the condition of the germplasm. Thus, any breeding methods using the inbred corn line NPFF6228 are part of this invention: selfing, backcrosses, hybrid production, and crosses to populations, and haploid by such old and known methods of using KWS inducers lines, Krasnador inducers, stock six material that induces haploids and anther culturing and the like.

The present invention may be useful as a male-sterile plant. Sterility can be produced by pulling or cutting tassels from the plant, detasseling, use of gametocides, or use of genetic material to render the plant sterile using a CMS type of genetic control or a nuclear genetic sterility. Male sterility is employed in a hybrid production by eliminating the pollen shed from the seed producing parent. The seed producing parent is grown in isolation from other pollen sources except for the pollen source which is the male fertile inbred, which serves as the male parent in the hybrid. To facilitate pollination of the seed producing (female) parent, the male fertile inbreds are planted most often in rows near the male sterile (female) inbred.

Methods for genetic male sterility are disclosed in EPO 89/3010153.8, WO 90/08828, U.S. Pat. Nos. 4,654,465, 4,727,219, 3,861,709, 5,432,068 and 3,710,511. Gametocides, some of which are taught in U.S. Pat. No. 4,735,649 (incorporated by reference) can be employed to make the plant male sterile. Gametocides including but not limited to glyphosate and its derivatives are chemicals or substances that negatively affect the pollen or at least the fertility of the pollen and provide male sterility to the seed producing parent.

Hybrid production employing any form of male sterility including mechanical emasculation tends to have a small occurrence of self pollinated female inbred seeds along with the intended F1 hybrid seeds. Great measures are taken to avoid the inbred seed production in a hybrid seed production field; but inbred seed unfortunately does occur in F1 seed production.

To detect inbred seed in a sample of putative hybrid seed the seeds can be tested with molecular markers, but another method is to plant the seed. The seed planting process is an inbred capture process which isolates inbred seed from hybrid F1 seed sources. This process for producing selected inbred seed comprises planting a group of seed comprising seed from a hybrid production, some of this seed may be seed of the hybrid parents. The inbred plants tend to be readily identifiable from the hybrid plants, the inbreds have a stunted appearance, i.e. shorter plant, smaller ear. Self pollination of the stunted plants grown from these identified inbred plants produces the female inbred seed or the hybrid. The resultant plants are observed for size or they can be tested by markers to identify any inbred plants. The identified inbred plants are selected and self-pollinated to form the inbred seed.

A number of well known methods can be employed to identify the genotype of maize. The ability to understand the genotype of the present invention increases as the technology moves toward better markers for identifying different components within the maize genetic material. One of the oldest methods is the use of isozymes which provides a generalized footprint of the material. Other markers adapted to provide a higher definition profile include Restriction Fragment Length Polymorphisms (RFLPs), Amplified Fragment Length Polymorphisms (AFLPs), Random Amplified Polymorphic DNAs (RAPDs), Polymerase Chain Reaction (there are different types of primers or probes) (PCR), Microsatellites (SSRs), and Single Nucleotide Polymorphisms (SNPs), sequence selection markers just to list a few. The use of these marker techniques for gathering genotype information from seeds and plants is well understood in the industry. The methods for using these techniques can be found in college textbooks such as Breeding Field Crops, Milton et. al. Iowa State University Press.

The marker profile of the inbred of this invention should be close to homozygous for alleles. A marker profile produced with any of the locus identifying systems known in the industry will identify a particular allele at a particular loci. A F1 hybrid made from the inbred of this invention will comprise a marker profile of the sum of both the profiles of its inbred parents. At each locus the allele for the present invention and the allele for the other inbred parent should be present. Thus the profile of the present invention will permit identification of hybrids as containing the inbred parent of the present invention. To identify the female portion of any hybrid the hybrid seed material from the pericarp which is maternally inherited is employed in a marker technique. The resultant profile is of the maternal parent. The comparison of this maternal profile with the hybrid profile will allow identification of the paternal profile. The present invention includes a maize cell that is part of an inbred or hybrid plant which includes its seed or plant part that has the marker profile of alleles of the present invention.

Marker systems are not just useful for identification of the present invention; they are also useful for breeding and trait conversion techniques. Polymorphisms in maize permit the use of markers for linkage analysis. If SSR are employed with flanking primers, the marker profile can be developed with PCR and Southern Blots can often be eliminated. Use of flanking markers, PCR and amplification to genotype maize matured of the material is well known by the industry. Primers for SSR markers and maize genome mapping information are publicly available through the help of the USDA at Maize GDB on the web.

Marker profiles of this invention can be employed to identify essentially derived varieties or progeny developed with the inbred in its ancestry. This inbred may have progeny identified by having a molecular marker profile with genetic contribution of the present inbred invention, as measured by either percent identity or percent similarity.

The present invention may have a new locus or trait introgressed through direct transformation, breeding methods including but not limited to backcrossing or marker assisted breeding. A backcross conversion or locus conversion both refer to a product of a backcrossing program.

The use of the present inbred as a recurrent parent in a breeding program it is often referred to as backcrossing. Backcrossing is often employed to introgression a desired trait or trait(s), either transgenic or nontransgenic, into the recurrent parent. A plant with the trait or the desired locus is crossed into recurrent maize parent usually in one or more backcrosses. If markers are employed to assist in selection of progeny that have the desired trait and recurrent parent backround genectics, then the number of backcrosses needed to recover the recurrent parent with the desired trait or locus can be relatively few two or three. However, 3, 4, 5 or more backcrosses are often required to produce the desired inbred with the gene or loci conversion in place. The number of backcrosses needed for a trait introgression is often linked to the genetics of the line carrying the trait and the recurrent parent and the genetics of the trait. Multigenic traits, recessive alleles, unlinked traits play a role in the number of backcrosses that may be necessary to achieve the desired backcross conversion of the inbred.

In a book written by Hallauer entitled Corn and Corn Improvement, Sprague and Dudley, 3rd Ed. 1998 the basics of maize crossing techniques along with a number of other corn breeding methods such as recurrent, bulk or mass selection, pedigree breeding, open pollination breeding, marker assisted selection, double haploids development and selection breeding are taught. The ordinary corn breeder understands these breeding systems and how to apply such techniques to the present invention. Therefore, repetition of how to perform these breeding methods is not listed within this application.

Dominant, single gene traits or traits with obvious phenotypic changes are particularly well managed in backcrossing programs. Prior to transformation and prior to markers, backcrossing was employed since the 1950's to breed in identified maize traits.

The backcrossing program is more complicated when the trait is a recessive gene. To determine the presence of the recessive gene requires the use of some testing to determine if the trait I has been transferred. Use of markers to detect the gene reduces the complexity of trait identification in the progeny. A marker that is a SNP, specific for the trait, can increase the efficiency and speed of tracking a recessive trait within a backcrossing program. Backcrossing of recessive traits has allowed known mutation traits to be moved into more elite germplasm. Mutations can be induced in germplasm by the plant breeder. Mutations can also result from plant or seed or pollen exposure to temperature alterations, culturing, radiation in various forms, chemical mutagens like EMS and others. Some of the mutant genes which have been identified and introgressed into elite maize include the genotypes: waxy (wx), amylose extender (ae), dull (du), horny (h), shrunken (sh), brittle (bt), floury (fl), opaque (o), and sugary (su). Nomenclature for mutant genes is based on the effect these mutant genes have on the physical appearance and phenotype of the kernel. There are mutant genes which produce starch with markedly different functional properties even though the phenotypes of the seed and plant remain the same. Mutant subspecies *have* generally been given a number after the named genotype, for example, sugary-1 (su1), sugary-2 (su2); shrunken 1 (sh1) and shrunken 2 (sh2). Traits such as Ht, waxy, brown mid-rib, amaylose, amlyose brown mid-rib, amylose extender (ae), opaque, dull, imazethapyr tolerant (IT or IR-designations for two different imazethapyr resistant genes), sterility, fertility, phytic acid, NLB, SLB, and the like have all been introgressed into elite inbreds through breeding programs. The last backcross generation is usually selfed if necessary to recover the inbred of interest with the introgressed trait.

All plants and plant cells produced using inbred corn line NPFF6228 are within the scope of this invention. The invention encompasses the inbred corn line used in crosses with other, different, corn inbreds to produce (F1) corn hybrid seeds and hybrid plants and the grain produced on the hybrid plant. This invention includes plant and plant cells, which upon growth and differentiation produce corn plants having the physiological and morphological characteristics of the inbred line NPFF6228.

This invention also includes transforming of introgressed transgenic genes, or specific locus into the present invention. The prior art has an extended list of transgenes, and of specific locus that carry desirable traits. The transgenes that can be introgressed include but are not limited to insect resistant genes such as Corn Rootworm gene(s) in the event DAS-59122-7, Mir603 Modified Cry3A event, MON 89034, MON 88017 *Bacillus thuringiensis* (Cry genes) Cry34/35Ab1, Cry1A.105, PO Cry1F, Cry2Ab2, Cry1A, Cry1AB, Cry1Ac Cry3Bb1, or herbicide resistant genes such as Pat gene or Bar gene, EPSP, the altered protoporphyrinogen oxidase (protox enzyme) U.S. Pat. Nos. 5,767,373, 6,282,837, WO 01/12825, or disease resistant genes such as the Mosaic virus resistant gene, etc., or trait altering genes such as lignin genes, flowering genes, oil modifying genes, senescence genes and the like.

The present invention also encompasses the addition of traits that focus on products or by products of the corn plant such as the sugars, oils, protein, ethanol, biomass and the like. The present invention can include a trait that forms an altered carbohydrate or altered starch. An altered carbohydrate or altered starch can be formed by an introgressed gene(s) that affect the synthase, branching enzymes, pullanases, debranching enzymes, isoamylases, alpha amylases, beta amylases, AGP, ADP and other enzymes which effect the amylose, and or amylopectin ratio or content or the branching pattern of starch. The fatty acid modifying genes if introgressed into the present invention can also affect starch content. Additionally, introgressed genes that are associated with or effect the starch and carbohydrates can be adapted so that the gene or its enzyme does not necessarily alter the form or formation of the starch or carbohydrate of the seed or plant; instead the introgressed gene or its RNA, polypeptide, protein or enzyme adapted to degrade, alter, or otherwise change the formed starch or carbohydrate. Examples of this technology are shown in U.S. Pat. Nos. 7,033,627, 5,714,474, 5,543,570, 5,705,375, 7,102,057, which are incorporated by reference. An example of use of an alpha amylase adapted in this manner in maize is shown in U.S. Pat. No. 7,407,677 which is also incorporated by reference.

The methods and techniques for inserting, or producing and/or identifying a mutation or making or reshuffling a transgene and introgressing the trait or gene into the present invention through breeding, transformation, mutating and the like are well known and understood by those of ordinary skill in the art.

Various techniques for breeding, moving or altering genetic material within or into the present invention (whether it is an inbred or in hybrid combination) are also known to those skilled in the art. These techniques to list only a few are anther culturing, haploid/double haploid production, (stock six, which is a breeding/selection method using color markers and is a method that has been in use for forty years and is well known to those with skill in the art), transformation, irradiation to produce mutations, chemical or biological mutation agents and a host of other methods are within the scope of the invention. All parts of the NPFF6228 plant including its plant cells produced using the inbred corn line are within the scope of this invention. The term transgenic plant refers to plants having genetic sequences, which are introduced into the genome of a plant by a transformation method and the progeny thereof. Transformation methods are means for integrating new genetic coding sequences into the plant's genome by the incorporation of these sequences into a plant through man's assistance, but not by breeding practices. The transgene once introduced into plant material and integrated stably can be moved into other germplasm by standard breeding practices.

The recombinant DNA molecules of the invention can be introduced into the plant cell in a number of art-recognized ways. Suitable methods of transforming plant cells include microinjection (Crossway et al., BioTechniques 4:320-334 (1986)), electroporation (Riggs et al, Proc. Natl. Acad. Sci. USA 83:5602-5606 (1986)), *agrobacterium* mediated transformation (Hinchee et al., Biotechnology 6:915-921 (1988)), direct gene transfer (Paszkowski et al., EMBO J. 3:2717-2722 (1984)), ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., Biotechnology 6:923-926 (1988)), protoplast transformation/regeneration methods (see U.S. Pat. No. 5,350,689 issued Sep. 27, 1994 to Ciba-Geigy Corp.), Whiskers technology (See U.S. Pat. numbers 5,464,765 and 5,302,523) and pollen transformation (see U.S. Pat. No. 5,629,183). Also see, Weissinger et al., Annual Rev. Genet. 22:421-477 (1988); Sanford et al., Particulate Science and Technology 5:27-37 (1987)(onion); Christou et al., Plant Physiol. 87:671-674 (1988) (soybean); McCabe et al., Bio/Technology 6:923-926 (1988) (soybean); Datta et al., Bio/Technology 8:736-740 (1990) (rice); Klein et al., Proc. Natl. Acad. Sci. USA, 85:4305-4309 (1988) (maize); Klein et al., Bio/Technology 6:559-563 (1988) (maize); Klein et al., Plant Physiol. 91:440-444 (1988) (maize); Fromm et al., Bio/Technology 8:833-839 (1990); Gordon-Kamm et al., Plant Cell 2:603-618 (1990) (maize); and U.S. Pat. Nos. 5,591,616 and 5,679,558 (Rice).

Vectors can include such items as: leader sequences, transit polypeptides, promoters, terminators, genes, introns, marker genes, etc. The structures of the gene orientations can be sense, antisense, partial antisense, or partial sense: multiple gene copies can be used. The transgenic gene can come from various non-plant genes (such as; bacteria, yeast, animals, and viruses) along with being from plants.

The DNA is then transformed into the plant. A transgene introgressed into this invention typically comprises a nucleotide sequence whose expression is responsible or contributes to the trait under the control of a promoter appropriate for the expression of the nucleotide sequence at the desired time in the desired tissue or part of the plant. Constitutive or inducible promoters are used. The transgene may also comprise other regulatory elements such as for example translation enhancers or termination signals. In an embodiment, the nucleotide sequence is the coding sequence of a gene and is transcribed and translated into a protein. In another embodiment, the nucleotide sequence encodes an antisense RNA, a sense RNA that is not translated or only partially translated, a t-RNA, a r-RNA or a sn-RNA.

Where more than one trait is introgressed into this invention, it is that the specific genes are all located at the same genomic locus in the donor, non-recurrent parent, preferably, in the case of transgenes, as part of a single DNA construct integrated into the donor's genome. Alternatively, if the genes are located at different genomic loci in the donor, non-recurrent parent, backcrossing allows to recover all of the morphological and physiological characteristics of the invention in addition to the multiple genes in the resulting maize inbred line.

In an embodiment, a transgene whose expression results or contributes to a desired trait to be transferred to the present invention comprises a virus resistance trait such as, for example, a MDMV strain B coat protein gene whose expression confers resistance to mixed infections of maize dwarf mosaic virus and maize chlorotic mottle virus in transgenic maize plants (Murry et al. Biotechnology (1993) 11:1559 64). In another embodiment, a transgene comprises a gene encoding an insecticidal protein, such as, for example, a crystal protein of *Bacillus thuringiensis* or a vegetative insecticidal protein from *Bacillus cereus*, such as VIP3 (see for example, Estruch et al. Nat Biotechnol (1997) 15:137 41). Also see, U.S. Pat. Nos. 5,877,012, 6,291,156; 6,107,279 6,291,156 and 6,429,360. In another embodiment, an insecticidal gene introduced into present invention is a Cry1Ab gene or a portion thereof, for example, introgressed into present invention from a maize line comprising a Bt-11 event as described in U.S. Pat. No. 6,114,608, which is incorporated herein by reference, or from a maize line comprising a 176 event as described in Koziel et al. (1993) Biotechnology 11: 194 200. In yet another embodiment, a transgene introgressed into present invention comprises a herbicide tolerance gene, for example, that is resistant to dicamba or a tolerance gene which provides of an altered acetohydroxyacid synthase (AHAS) enzyme confers upon plants tolerance to various imidazolinone or sulfonamide herbicides (U.S. Pat. No. 4,761,373). In another embodiment, a non-transgenic trait conferring tolerance to imidazolinones is introgressed into present invention (e.g. a "IT" or "IR" trait). U.S. Pat. No. 4,975,374, incorporated herein by reference, relates to plant cells and plants containing a gene encoding a mutant glutamine synthetase (GS) resistant to inhibition by herbicides that are known to inhibit GS, e.g. phosphinothricin and methionine sulfoximine. Also, expression of a *Streptomyces* bar gene encoding a phosphinothricin acetyl transferase in maize plants results in tolerance to the herbicide phosphinothricin or glufosinate (U.S. Pat. No. 5,489,520). U.S. Pat. No. 5,013,659, which is incorporated herein by reference, is directed to plants that express a mutant acetolactate synthase (ALS) that renders the plants resistant to inhibition by sulfonylurea herbicides. U.S. Pat. No. 5,162,602 discloses plants tolerant to inhibition by cyclohexanedione and aryloxyphenoxypropanoic acid herbicides. The tolerance is conferred by an altered acetyl coenzyme A carboxylase (ACCase). U.S. Pat. No. 5,554,798 discloses transgenic glyphosate tolerant maize plants, which tolerance is conferred by an altered 5-enolpyruvyl-3-phosphoshikimate (EPSP) synthase gene. U.S. Pat. No. 5,804,425 discloses transgenic glyphosate tolerant maize plants, which tolerance is conferred by an EPSP synthase gene derived from *Agrobacterium tumefaciens* CP-4 strain. Also, tolerance to a protoporphyrinogen oxidase inhibitor is achieved by expression of a tolerant protoporphyrinogen oxidase enzyme in plants (U.S. Pat. No. 5,767,373). Another trait transferable to the present invention confers a safening effect or additional tolerance to an inhibitor of the enzyme hydroxyphenylpyruvate dioxygenase (HPPD) and transgenes conferring such trait are, for example, described in WO 9638567, WO 9802562, WO 9923886, WO 9925842, WO 9749816, WO 9804685 and WO 9904021. All issued patents referred to herein are, in their entirety, expressly incorporated herein by reference.

In an embodiment, a transgene transferred to present invention comprises a gene conferring tolerance to a herbicide and at least another nucleotide sequence encoding another trait, such as for example, an insecticidal protein. Such combination of single gene traits is, for example, a Cry1Ab gene and a bar gene. The introgression of a Bt11 event into a maize line, such as present invention, by backcrossing is exemplified in U.S. Pat. No. 6,114,608, and the present invention is directed to methods of introgressing a Bt11 event into present invention and to progeny thereof using for example the markers described in U.S. Pat. No. 6,114,608.

By way of example only, specific events (followed by their APHIS petition numbers) that can be introgressed into maize plants by backcross breeding techniques include the glyphosate tolerant event GA21 (97-09901p) or the glyphosate tolerant event NK603 (00-011-01p), the glyphosate tolerant/Lepidopteran insect resistant event MON 802 (96-31701p) Mon810, Lepidopteran insect resistant event DBT418 (96-29101p), male sterile event MS3 (95-22801p), Lepidopteran insect resistant event Bt11 (95-19501p), phosphinothricin tolerant event B16 (95-14501p), Lepidopteran insect resistant event MON 80100 (95-09301p) and MON 863 (01-137-01p), phosphinothricin tolerant events T14, T25 (94-35701p), Lepidopteran insect resistant event 176 (94-31901p), Western corn rootworm (04-362-01p), the phosphinothricin tolerant and Lepidopteran insect resistant event CBH-351 (92-265-01p), and the transgenic corn event designated 3272 taught in US application publication 20060230473 (hereby incorporated by reference).

A further subject of the present invention is the plants which comprise transformed cells, in particular the plants regenerated from transformed cells. Regeneration is effected by any suitable process, which depends on the nature of the species as described, for example, in the references hereinabove. Patents and patent applications which are cited in particular for the processes for transforming plant cells and regenerating plants are the following: U.S. Pat. Nos. 4,459, 355, 4,536,475, 5,464,763, 5,177,010, 5,187,073, EP 267, 159, EP 604 662, EP 672 752, U.S. Pat. Nos. 4,945,050, 5,036,006, 5,100,792, 5,371,014, 5,478,744, 5,179,022, 5,565,346, 5,484,956, 5,508,468, 5,538,877, 5,554,798, 5,489,520, 5,510,318, 5,204,253, 5,405,765, EP 442 174, EP 486 233, EP 486 234, EP 539 563, EP 674 725, WO 91/02071 and WO 95/06128.

The use of pollen, cotyledons, zygotic embryos, meristems and ovum as the target tissue can eliminate the need for extensive tissue culture work. Generally, cells derived from meristematic tissue are useful. The method of transformation of meristematic cells of cereal is taught in the PCT application WO96/04392. Any number of various cell lines, tissues, calli and plant parts can and have been transformed by those having knowledge in the art. Methods of preparing callus or protoplasts from various plants are well known in the art and specific methods are detailed in patents and references used by those skilled in the art. Cultures can be initiated from most of the above-identified tissue. The only true requirement of the transforming plant material is that it can ultimately be used to form a transformed plant.

Duncan, Williams, Zehr, and Widholm, Planta (1985) 165: 322 332 reflects that 97% of the plants cultured that produced callus were capable of plant regeneration. Subsequent experiments with both inbreds and hybrids produced 91% regenerable callus that produced plants. In a further study in 1988, Songstad, Duncan & Widholm in Plant Cell Reports (1988), 7:262 265 reports several media additions that enhance regenerability of callus of two inbred lines. Other published reports also indicated that "nontraditional" tissues are capable of producing somatic embryogenesis and plant regeneration. K. P. Rao, et al., Maize Genetics Cooperation Newsletter, 60:64 65 (1986), refers to somatic embryogenesis from glume callus cultures and B. V. Conger, et al., Plant Cell Reports, 6:345 347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture procedures of maize are described in Green and Rhodes, "Plant Regeneration in Tissue Culture of Maize," Maize for Biological Research (Plant Molecular Biology Association, Charlottesville, Va. 1982, at 367 372) and in Duncan, et al., "The Production of Callus Capable of Plant Regeneration from Immature Embryos of Numerous *Zea mays* Genotypes," 165 Planta 322 332 (1985). Thus, another aspect of this invention is to provide cells that upon growth and differentiation produce maize plants having the physiological and morphological characteristics of the present invention.

Maize is used as human food, livestock feed, and as raw material in industry. Sweet corn kernels having a relative moisture of approximately 72% are consumed by humans and may be processed by canning or freezing. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry. Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications. Plant parts other than the grain of maize are also used in industry: for example, stalks and husks are made into paper and wallboard and cobs are used for fuel and to make charcoal.

The seed of the present invention or of the present invention further comprising one or more single gene traits, the plant produced from the inbred seed, the hybrid maize plant produced from the crossing of the inbred, hybrid seed and various parts of the hybrid maize plant, can be utilized for human food, livestock feed, and as a raw material in industry.

The present invention therefore also discloses an agricultural product comprising a plant of the present invention or derived from a plant of the present invention. The present invention also discloses an industrial product comprising a plant of the present invention or derived from a plant of the present invention. The present invention further discloses methods of producing an agricultural or industrial product comprising planting seeds of the present invention, growing plant from such seeds, harvesting the plants and processing them to obtain an agricultural or industrial product.

A deposit of at least 2500 seeds of this invention will be maintained by Syngenta Seeds Inc. Access to this deposit will be available during the pendency of this application to the Commissioner of Patents and Trademarks and persons determined by the Commissioner to be entitled thereto upon request. All restrictions on availability to the public of such material will be removed upon issuance of a granted patent of this application by depositing at least 2500 seeds of this invention at the American Type Culture Collection (ATCC), at 10801 University Boulevard, Manassas, Va. 20110. The ATCC number of the deposit is PTA-13583. The date of deposit was Feb. 28, 2013 and the seed was tested on Mar. 19, 2013 and found to be viable. The deposit of at least 2500 seeds will be from inbred seed taken from the deposit maintained by Syngenta Seeds Inc. The ATCC deposit will be maintained in that depository, which is a public depository, for a period of 30 years, or 5 years after the last request, or for the enforceable life of the patent, whichever is longer, and will be replaced if it becomes nonviable during that period.

Additional public information on patent variety protection may be available from the PVP Office, a division of the U.S. Government.

Accordingly, the present invention has been described with some degree of particularity directed to the embodiment of the present invention. It should be appreciated, though that the present invention is defined by the following claims construed in light of the prior art so that modifications or changes may be made to the embodiment of the present invention without departing from the inventive concepts contained herein.

Variety Description Information
1 Type: Dent
2 Region Best Adapted:—Broadly adapted

| *MG Group | Maturity Range | Hybrid RM*(estimate) |
|---|---|---|
| 6 | 108-112 | 115 |

*MG = Maturity group
**Maturity is the number of days from planting to physiological maturity (planting to black layer)
***RM = relative maturity

3.

| Line | Anther | Glume color | SilkColor | BraceRootColor | CobColor | KernelColor | Endosperm Type |
|---|---|---|---|---|---|---|---|
| NPFF6228 | Yellow | Green | Yellow | Moderate | Red | Yellow | |
| Inbred1 | Pink | Green | Green | Moderate | Pink | Yellow | Normal |

4.

Plant Disease Traits

| Line | Carbonum | Common Rust | Eyespot | Goss' Wilt | GLS | NCLB | SCLB |
|---|---|---|---|---|---|---|---|
| NPFF6228 | | | MS | MR | MS | R | MR |
| Inbred1 | R | MS | MR | R | MS | R | MR |

The data provided above is often a color. The Munsell code is a reference book of color, which is known and used in the industry and by persons with ordinary skill in the art of plant breeding. The purity and homozygosity of inbred NPFF6228 is constantly being tracked using isozyme genotypes. Isozyme data can be generated for inbred corn line NPFF6228 according to procedures known and published in the art.

Isozyme Genotypes for NPFF6228

Isozyme data were generated for inbred corn line NPFF6228 according to procedures known and published in the art. The data in the Electrophoresis Table gives the electrophoresis data on NPFF6228.

| ELECTROPHORESIS RESULTS FOR NPFF6228 | | | | | | | | | | | |
|---|---|---|---|---|---|---|---|---|---|---|---|
| Line | PGM1 | PGM2 | PGD1 | PGD2 | IDH1 | IDH2 | MDH1 | MDH2 | MDH3 | MDH4 | MDH5 |
| NPFF6228 | 9 | 3 | 2 | 2.8 | 4 | 4 | 6 | 3 | 16 | 12 | 12 |
| Inbred1 | 9 | 4 | 3.8 | 5 | 4 | 4 | 6 | 3 | 16 | 12 | 12 |

| Line | MDH6 | ACP1 | ACP4 | GLU | PHI | CAT3 | DIA1 | GOT1 | GOT2 | GOT3 | ADH |
|---|---|---|---|---|---|---|---|---|---|---|---|
| NPFF6228 | Mm | 2 | 2 | 0 | 4 | 0 | 0 | 0 | 0 | 0 | 4 |
| Inbred1 | Mm | 2 | 2 | . | 4 | 0 | 0 | 0 | 0 | 0 | 0 |

The Paired Inbred Comparison Data Table A show a comparison between NPFF6228 and comparable inbreds.

| THE PAIRED INBRED COMPARISON DATA TABLE A | | | | | | |
|---|---|---|---|---|---|---|
| Inbred | Yield | Stand | HeatUnits to P50 | HeatUnits to S50 | Plant Height | Ear Height |
| NPFF6228 | 120.4 | 34611.1 | 1382.9 | 1403.1 | 74.4 | 36.9 |
| Inbred1 | 122.4 | 33708.3 | 1422.8 | 1451.1 | 76.1 | 38.1 |
| Diff | 6.7 | 458.3 | 39.9 | 48 | 2.7 | 2.5 |
| # Expts | 6 | 6 | 18 | 17 | 5 | 5 |
| Prob | 0.377 | 0.454 | 0.001*** | 0.000*** | 0.128 | 0.158 |

| Inbred | % Large Rounds | % Large Flats | % Med. Rounds | % Med. Flats | % Small Rounds | % Small Flats | Shed Duration | Pollen Count |
|---|---|---|---|---|---|---|---|---|
| NPFF6228 | 11.4 | 1.6 | 1.6 | 1.6 | 26.6 | 52.1 | | |
| Inbred1 | 28.5 | 6.2 | 0.4 | 0.6 | 15 | 43.6 | 165.7 | 725037 |
| Diff | | | | | | | | |
| # Expts | | | | | | | | |
| Prob | | | | | | | | |

*.05 < Prob <= .10
**.01 < Prob <= .05
***.00 < Prob <= .01

The General Combining Ability Table shows the GCA (General Combining Ability) estimates of NPFF6228 compared with the GCA estimates of the other inbreds. The estimates show the general combining ability is weighted by the number of experiment/location combinations in which the specific hybrid combination occurs. The interpretation of the data for all traits is that a positive comparison is a practical advantage. A negative comparison is a practical disadvantage.

The general combining ability of an inbred is clearly evidenced by the results of the general combining ability estimates. This data compares the inbred parent in a number of hybrid combinations to a group of "checks". The check data is from our company's and other companies' hybrids which are commercial products and pre-commercial hybrids, which were grown in the same sets and locations.

| GCA TABLE | | | | | | | | | | |
|---|---|---|---|---|---|---|---|---|---|---|
| Line | N | Yield | Moisture | TestWeight | % Stalk Lodging | % Push Test | % Late Root Lodging | % Early Root Lodging | % Dropped Ears | Final Stand |
| NPFF6228 | 138 | 5.8 | −0.81 | −0.41 | −0.29 | −0.97 | 2.58 | 2.58 | 0.01 | −0.46 |
| XR = | 138 | 5.8 | −0.81 | −0.41 | −0.29 | −0.97 | 2.58 | 2.58 | 0.01 | −0.46 |
| XH = | 1 | 5.8 | −0.81 | −0.41 | −0.29 | −0.97 | 2.58 | 2.58 | 0.01 | −0.46 |
| XT = | 1 | 5.8 | −0.81 | −0.41 | −0.29 | −0.97 | 2.58 | 2.58 | 0.01 | −0.46 |

| Line | Stay Green % | % Green Snap | % Barren | Emergence Rating | Vigor Rating | Heatunits to S50 | Heatunits to P50 | Ear Height | Plant Height |
|---|---|---|---|---|---|---|---|---|---|
| NPFF6228 | 4.51 | −1.36 | −0.52 | −0.19 | 0.09 | −25.75 | −25.47 | 2 | −3.79 |
| XR = | 4.51 | −1.36 | −0.52 | −0.19 | 0.09 | −25.75 | −25.47 | 2 | −3.79 |
| XH = | 4.51 | −1.36 | −0.52 | −0.19 | 0.09 | −25.75 | −25.47 | 2 | −3.79 |
| XT = | 4.51 | −1.36 | −0.52 | −0.19 | 0.09 | −25.75 | −25.47 | 2 | −3.79 |

The Paired Hybrid Comparison Data Table A through B shows the inbred NPFF6228 in hybrid combination, as Hybrid 1, in comparison with another hybrid, which is adapted for the same region of the Corn Belt.

| PAIRED HYBRID COMPARISON DATA TABLE A | | | | | | | | |
|---|---|---|---|---|---|---|---|---|
| Hybrid | Yield | Moist | TWT | PCTERL | PCTSL | PCTPUSH | PLTLRL | PCTDE |
| Hybrid1 w/ NPFF62282 | 211.7 | 23.4 | 53.8 | 4.7 | 4 | 25.9 | 1.9 | 0 |
| Hybrid2 | 209.6 | 23 | 53.9 | 13.6 | 7.8 | 23.3 | 5.9 | 0 |
| # Expts | 160 | 160 | 64 | 11 | 70 | 15 | 41 | 11 |
| Diff | 2.1 | 0.4 | 0.1 | 8.9 | 3.9 | 2.5 | 4 | 0 |
| Prob | 0.23 | 0.001*** | 0.911 | 0.113 | 0.063* | 0.693 | 0.019** | |
| Hybrid | Stand | PCTSG | PCTGS | PctBarren | Emerge | Vigor | HUS50 | |
| Hybrid1 w/ NPFF6228 | 203.9 | 11.7 | 0.6 | | 3.3 | 3.7 | 1326 | |
| Hybrid2 | 206.5 | 8.7 | 5.4 | | 3.4 | 3.7 | 1338 | |
| # Expts | 167 | 3 | 18 | | 31 | 41 | 15 | |
| Diff | 2.6 | 3 | 4.8 | | 0.1 | 0 | 11.2 | |
| Prob | 0.029** | 0.483 | 0.115 | | 0.712 | 0.923 | 0.298 | |
| Hybrid | HUP50 | Pltht | Earht | | | | | |
| Hybrid1 w/ NPFF6228 | 1319 | 261.6 | 121.2 | | | | | |
| Hybrid2 | 1339 | 273.4 | 125.3 | | | | | |
| # Expts | 13 | 26 | 26 | | | | | |
| Diff | 20 | 11.7 | 4.1 | | | | | |
| Prob | 0.103 | 0.000*** | 0.055* | | | | | |

*.05 < Prob <= .10

**.01 < Prob <= .05

***.00 < Prob <= .01

| PAIRED HYBRID COMPARISON DATA TABLE B | | | | | | | | |
|---|---|---|---|---|---|---|---|---|
| Hybrid | Yield | Moist | TWT | PCTERL | PCTSL | PCTPUSH | PLTLRL | PCTDE |
| Hybrid1 w/ NPFF6228 | 214.1 | 23.6 | 53.5 | 5.2 | 0.6 | 26.3 | 0.6 | 0 |
| Hybrid3 | 211.3 | 23.8 | 53.4 | 15 | 0.4 | 7.4 | 7 | 0 |
| # Expts | 59 | 65 | 31 | 5 | 26 | 7 | 13 | 1 |
| Diff | 2.9 | 0.2 | 0.1 | 9.8 | 0.2 | 18.9 | 6.4 | 0 |
| Prob | 0.258 | 0.284 | 0.782 | 0.253 | 0.305 | 0.054* | 0.116 | |
| Hybrid | Stand | PCTSG | PCTGS | PctBarren | Emerge | Vigor | HUS50 | |
| Hybrid1 w/ NPFF6228 | 238.7 | | 0.6 | | 3.4 | 3.6 | 1298 | |
| Hybrid3 | 237.6 | | 1.3 | | 3.5 | 3.2 | 1306 | |
| # Expts | 67 | | 6 | | 14 | 17 | 5 | |
| Diff | 1.1 | | 0.7 | | 0.1 | 0.4 | 8.2 | |
| Prob | 0.63 | | 0.335 | | 0.546 | 0.111 | 0.431 | |
| Hybrid | HUP50 | Pltht | Earht | | | | | |
| Hybrid1 w/ NPFF6228 | 1296 | 259.4 | 122.3 | | | | | |
| Hybrid3 | 1306 | 270.3 | 126.1 | | | | | |
| # Expts | 5 | 11 | 11 | | | | | |
| Diff | 10.6 | 10.9 | 3.8 | | | | | |
| Prob | 0.311 | 0.021** | 0.409 | | | | | |

The Yield by Environment Response Table shows the yield response of Hybrid 1 w/NPFF6228 as a parent in comparison with two other hybrids and the plants in the environment around it at the same location.

| Yield By Environment Response Table | | | | | | | | |
|---|---|---|---|---|---|---|---|---|
| Research Plots | | | Environment Yield | | | | | |
| Hybrid | Error | # Plots | 75 | 100 | 125 | 150 | 175 | 200 |
| Hybrid1 w/ NPFF6228 | 19.9 | 138 | 94 | 118 | 142 | 165 | 189 | 213 |
| Hybrid2 | 22.3 | 1164 | 98 | 122 | 146 | 170 | 193 | 217 |
| Research Plots | | | Environment Yield | | | | | |
| Hybrid | Error | # Plots | 75 | 100 | 125 | 150 | 175 | 200 |
| Hybrid1 w/ NPFF6228 | 19.9 | 138 | 94 | 118 | 142 | 165 | 189 | 213 |
| Hybrid3 | 18.4 | 120 | 81 | 107 | 134 | 160 | 186 | 212 |
| Strip Tests | | | Environment Yield | | | | | |
| Hybrid | Error | # Strips | 75 | 100 | 125 | 150 | 175 | 200 |
| Hybrid1 w/ NPFF6228 | 1 | 66 | 77 | 104 | 130 | 156 | 182 | 208 |
| Hybrid2 | 1.2 | 284 | 77 | 103 | 128 | 154 | 180 | 205 |
| Strip Tests | | | Environment Yield | | | | | |
| Hybrid | Error | # Strips | 75 | 100 | 125 | 150 | 175 | 200 |
| Hybrid1 w/ NPFF6228 | 1 | 66 | 77 | 104 | 130 | 156 | 182 | 208 |
| Hybrid3 | 1.5 | 97 | 77 | 103 | 129 | 155 | 180 | 206 |

Accordingly, the present invention has been described with some degree of particularity directed to the embodiment of the present invention. It should be appreciated, though that the present invention is defined by the following claims construed in light of the prior art so that modifications or changes may be made to the embodiment of the present invention without departing from the inventive concepts contained herein.

I claim:

1. A seed of the maize variety NPFF6228, representative seed of said variety having been deposited under ATCC Accession Number PTA-13583.

2. A maize plant of maize variety NPFF6228, representative seed of said variety having been deposited under ATCC Accession Number PTA-13583.

3. An F1 hybrid maize seed produced by crossing a maize plant variety NPFF6228 according to claim 2 with itself or a different maize plant.

4. A maize plant part of the plant of claim 2.

5. A maize plant part according to claim 4 comprising a seed.

6. A maize plant or its parts produced by growing the F1 hybrid maize seed of claim 3.

7. A cell from a maize tissue culture of regenerable cells of the plant of claim 2.

8. A method of producing a maize plant variety NPFF6228 with a desired trait into comprising: (a) crossing a NPFF6228 plant according to claim 2, with a plant of another maize line that comprises the desired trait to produce F1 progeny plants, wherein the desired trait is selected from the group consisting of waxy starch, amylase, male sterility, modified carbohydrates, modified corn fiber, modified fatty acids metabolism, modified fatty acids, herbicide resistance, insect resistance, bacterial disease resistance, fungal disease resistance, and viral disease resistance; (b) selecting F1 progeny plants that have the desired trait to produce selected F1 progeny plants; (c) crossing the selected progeny plants with the NPFF6228 plants to produce backcross progeny plants; (d) selecting for backcross progeny plants that have the desired trait to produce selected desired progeny plants; and (e) repeating steps (c) and (d) at least one more times to produce plants that comprise the desired trait and all of the physiological and morphological characteristics of maize plant variety NPFF6228 when grown in the same environmental conditions.

9. A maize seed from a derived maize variety NPFF6228 produced by the process of claim 8.

10. A method of producing a plant byproduct comprising obtaining the plant of claim 6 or a part thereof and producing said plant byproduct therefrom.

11. A process of producing maize seed comprising a transgene encoding an amylase, comprising crossing a first parent maize plant according to claim 2 with a second parent maize plant with said transgene, and harvesting the resultant seed.

12. The maize seed according to claim 5 further comprising a transgene.

13. The maize seed of claim 12, wherein the maize seed is hybrid seed.

14. A method of producing a second maize plant comprising introducing a transgene or trait allele conferring a desired trait into the plant of maize variety NPFF6228 according to claim 2, and wherein said introduction results in the production of said second maize plant.

15. The method of claim 14 wherein the desired trait is herbicide resistance, selected from a group comprising: glyphosate, sulfonylurea, imidazolinone, dicamba, glufosinate, phenoxypropionic acid, cyclohexanedione, triazine, benzonitrile and bromoxynil.

16. The second maize plant produced by the method of claim 14, wherein the gene confers a trait selected from the group consisting of herbicide tolerance; insect tolerance; resistance to bacterial, fungal, nematode or viral disease; waxy starch; male sterility and restoration of male fertility, modified carbohydrate metabolism and modified fatty acid metabolism.

17. A method of producing a maize plant derived from the variety NPFF6228, the method comprising the steps of (a) growing a progeny plant produced by crossing the plant of claim 2 with a second maize plant; (b) crossing the progeny plant with itself or a different plant to produce a seed of a progeny plant of a subsequent generation; (c) growing a progeny plant of an earlier generation from said seed and crossing the progeny plant of a subsequent generation with itself or a different plant; and (d) repeating steps (b) and (c) for an additional 0-5 generations to produce a maize plant derived from the variety NPFF6228.

18. A method of claim 10 wherein the plant byproduct is silage, starch, ethanol, oil, syrup, meal, amylase, or protein.

19. A method for developing a maize derived plant from the plant of claim 2 comprising the steps of crossing the plant of claim 2 with at least one other plant to form a plant population; breeding said plant population with plant breeding techniques selected from the group consisting of recurrent selection, backcrossing, pedigree breeding, genetic marker enhanced selection, and double haploid breeding, forming breeding progeny, and selecting maize derived plants from said breeding progeny.

* * * * *